US008033186B2

(12) United States Patent
Berndtsson et al.

(10) Patent No.: US 8,033,186 B2
(45) Date of Patent: Oct. 11, 2011

(54) DEVICE FOR EXTRACTION OF A PARTIALLY DEFINED SAMPLE VOLUME FROM A LARGER VOLUME (75) Inventors: Ingemar Berndtsson, Sollentuna (SE); Tommy Andersson, Aloppevägen (SE)

(73) Assignee: Boule Medical AB, Stockholm (SE)

( * ) Notice: Subject to any disclaimer, the term of this patent is extended or adjusted under 35 U.S.C. 154(b) by 369 days.

(21) Appl. No.: 12/444,394

(22) PCT Filed: Sep. 24, 2007

(86) PCT No.: PCT/SE2007/000833
§ 371 (c)(1), (2), (4) Date: Apr. 5, 2009

(87) PCT Pub. No.: WO2008/041900
PCT Pub. Date: Apr. 10, 2008

(65) Prior Publication Data
US 2010/0101318 A1 Apr. 29, 2010

(30) Foreign Application Priority Data
Oct. 6, 2006 (SE) ...................................... 0602104

(51) Int. Cl.
*G01N 1/00* (2006.01)
(52) U.S. Cl. .......................................... 73/863; 600/573
(58) Field of Classification Search .......................... None
See application file for complete search history.

(56) References Cited

U.S. PATENT DOCUMENTS

| 4,978,624 | A | * | 12/1990 | Cremins et al. | ................. 436/17 |
| 5,536,643 | A | * | 7/1996 | Mock | ........................... 435/7.25 |
| 7,757,568 | B2 | * | 7/2010 | Shiraki | ...................... 73/861.15 |
| 2005/0009122 | A1 | | 1/2005 | Whelan et al. | |
| 2008/0287830 | A1 | * | 11/2008 | Voeller | .......................... 600/573 |
| 2010/0027868 | A1 | * | 2/2010 | Kosaka et al. | ................ 382/134 |
| 2010/0066996 | A1 | * | 3/2010 | Kosaka et al. | ................. 356/39 |
| 2011/0014645 | A1 | * | 1/2011 | Winkelman et al. | ............ 435/34 |

FOREIGN PATENT DOCUMENTS

SE 526330 8/2005
WO WO 99/44743 A1 9/1999

* cited by examiner

*Primary Examiner* — Andre Allen
(74) *Attorney, Agent, or Firm* — Greenblum & Bernstein, PLC

(57) ABSTRACT

The invention provides a device for extraction of a defined sample volume from a larger sample volume. The device includes a body having a reference surface and a measuring cavity extending from a part of the reference surface into the body, thereby forming at least one opening plane substantially uniform with the reference surface, the body being adapted for reception of an excess sample volume at the cavity and elimination of sample above the reference surface to leave in the cavity a measured sample volume having the defined volume. An information carrier is applied to or arranged for distribution with the device, having direct or indirect volume information about the defined volume established for the cavity. The invention also relates to a method for determining the volume of such a cavity, to a set of at least two such devices, to a method for dilution of at least two liquid samples by the use of at least two such devices, to an analytic instrument, to a method for operating such an instrument, to a system including the device and the instrument, and to a method for operating the system.

20 Claims, 6 Drawing Sheets

Fig. 1a

Prior art

Fig. 1b

Prior art

DEVICE FOR EXTRACTION OF A PARTIALLY DEFINED SAMPLE VOLUME FROM A LARGER VOLUME

CROSS-REFERENCE TO RELATED APPLICATIONS

The present application is a U.S. national stage application of PCT/SE2007/000833, filed 24 Sep. 2007, which claims the benefit of Swedish patent application 0602104-2, filed 6 Oct. 2006. Priority of the filing date of both of these is claimed, and the disclosures of both of these are incorporated herein by reference in their entireties.

BACKGROUND OF THE INVENTION

1. Field of the Invention

The present invention relates to a device for extraction of a partially defined sample volume from a larger liquid sample volume, to methods for determining the volume of at least one cavity of a device, to a set of at least two devices for dilution of liquid samples to the same or different defined degrees, to an analytic instrument for operative connection to a sample measuring and diluting device having at least one measuring cavity, and to a system having a sample measuring and diluting device and an analytical instrument.

2. Description of Related Art

In one type of blood testing, a system comprising a blood cell counting apparatus/analytical instrument provided with a blood sample volume defining device, preferably in the form of a disposable cassette, is used. To be able to count the blood cells in an accurate and repeatable way it is of crucial importance to define an accurate volume of a blood sample. The accurately defined volume of blood sample is normally diluted by an accurately defined volume of a diluent or a lysing agent, in order to obtain a dilution ratio of typically 1:100 to 1:80000. When counting white blood cells is concerned the dilution ratio is typically 1:400 and when counting red blood cells is concerned the dilution ratio is typically 1:40000, in the latter case the dilution often taking place in two steps. Thus, it is obvious that variations in sample volumes and dilution liquid volumes must be minimized such that a correct degree of dilution and counting of blood cells always can be guaranteed.

Apparently, obtaining the same sample volumes are a critical step in the dilution procedure, since the volumes concerned are extremely small compared to the corresponding diluent volumes. To be able to obtain an accurate dilution ratio of a blood sample it is of crucial importance that the cavity in which the blood sample is contained is filled in a very precise and accurate and repeatable way, and that the variations regarding the volume between different cavities having the same nominal volume are made as little as possible.

The Swedish patent application No. 0303157-2 describes a method and a device for defining a small volume of a larger liquid sample. The device includes a first body and a second body. In a surface thereof, the first body has at least one cavity having said defined volume, and the second body includes an edge relatively slidable along said surface and over the cavity thereby separating an excessive volume of sample from said surface, leaving a defined volume within the cavity.

By the non-published Swedish patent application No. 0500784-4 a sample volume defining device is known which comprises a sledge and a framework, movable relative to each other. The device forms a part of a disposable support, preferably in the form of a cassette, and the framework is formed integrally with said support. The support comprises at least two chambers, one of which is filled with an accurately defined volume of diluent or lysing agent for dilution of a liquid sample, preferably a blood sample, and the other is empty and thus used for achieving the dilution and mixing of the liquid sample. At least one accurately defined cavity is made in the sledge. The components of the device are preferably made by injection moulding.

Although all due care is take when said at least one cavity is made in the first body/sledge, which in the description below is called a sampling body/body, its volume will on one hand differ from sampling body to sampling body made by the same moulding tools as the tools wear, and so forth, and on the other hand from moulding tools to moulding tools. By knowing this volume variation between different cavities made in different sampling bodies, it is thus possible to even further improve the accuracy of the blood analyses when performing blood cell counting.

SUMMARY OF THE INVENTION

The object of the invention is to take these volume variations of the cavities into consideration when performing the blood analyses. This object is achieved by the devices, methods, and systems described herein.

BRIEF DESCRIPTION OF THE DRAWINGS

A non-limiting example of the present invention will be described hereinafter with reference to the accompanying drawings, wherein.

DETAILED DESCRIPTION OF VARIOUS EMBODIMENTS OF THE INVENTION

As indicated above, a sample volume defining device is known from WO 2005/052553 and the co-pending application SE 0303157-2, both incorporated by reference herein. Basically the known volume defining process incorporates a) application of a relatively larger, often undefined, volume of the sample, preferably liquids, onto a surface and into a cavity formed in the surface and b) moving a scraping edge over the surface to leave a smaller defined volume of the sample in the cavity. Further processing steps may follow, such as c) flushing the cavity with a liquid diluent, or dilution media, such as a solution or reagent, to obtain a diluted sample, d) mixing the sample and diluent to obtain a homogenous diluted sample and e) performing measurements on the diluted and mixed sample. The current invention builds on this known technology and represents a development thereof.

For purposes of discussion the surface can be regarded as a reference surface, comprising the physical surface as well as an "imaginary" surface, defining an opening plane for the cavity, the surface being flush and continuous with the physical surface, or defined in mechanical terms by movement of a thought entirely rigid scraper means in contact with the surface, across the cavity, also referred to as a "measuring cavity" herein, so as to define a volume of the cavity limited by the imaginary surface. The reference surface shall at least surround the cavity to such an extent as to allow the scraping action and preferably the reference surface encircles the cavity on all sides.

The reference surface may have different shapes as long as it meets the continuity requirement, consistent with the scraping purpose. For example, the reference surface with its cavity may be double-curved, meaning that it cannot be formed by bending a flat surface, as exemplified with a cavity in a ball valve, or the reference surface may preferably be single-curved, meaning that it can be formed from a flat surface, as exemplified by a cavity in a cylinder valve, or most preferably it is substantially flat, as exemplified by a cavity in a slide valve.

The cavity size, i.e. the volume under the imaginary surface, or rather the practical surface to be further discussed below, depends on several factors. Some of these factors are application dependent, such as sample nature and necessary volumes for planned dilution degrees or requirements for intended measurement. In disposable devices, for economical, reasons it is generally desirable to minimize the volumes in order also to minimize other features such as diluent volumes, mixing arrangements etc. However, manual manipulation and manufacturing constraints, e.g. moulding of plastics, may place a lower limit on practical or possible cavity sizes. In case of several cavities, e.g. for different dilution degrees, the restrictions typically are set by the smallest cavity. General values are difficult to give but experience has indicated that the cavity volume should preferably be larger than 0.01 microliter ($\mu$l), preferably larger than 0.05 and most preferable larger than 0.1 microliter. The maximum cavity volume can be kept below 50 microliter, preferably below 25 and most preferably below 15 microliter.

Similarly cavity shape may be determined by several factors. Besides manufacturing constraints that may place limits on advanced features of small cavities, desirable shape is mainly dictated by efficient filling and foreseeable, also expressed herein as reproducible, scraping results, of particular importance between different disposable devices.

Cavity filling may take place in various ways. As indicated, if a sample surplus is simply placed on the cavity there is a risk for gas inclusion and unfilled voids in the cavity. To avoid this the sample may be forced into the cavity, e.g. by a sample stream positively pumped by forced flow past the cavity, which, however, does not entirely secures flow through the cavity. Preferably then forced filling is made by insertion of a probe straight above or into the cavity, preferably with care taken against probe outlet contact and blocking, which cannot easily be compensated by increased injection pressure due to the hydraulic area relationship, and with necessary precision care needed for small cavities. For reasons given in the references a preferred filling method is use of capillary forces for filling. The criteria for capillary filling shall be regarded satisfied, and accordingly testable, if filling takes place, or can take place, without other forces applied.

The cavity may have several openings, or entrances, e.g. the cavity may form a tube extending between two openings as in known capillary tubes although here also connecting to a capillary driven filling channel. It is preferred, however, that to the extent the channel has more than one opening these opens into one and the same reference surface. Most preferably the cavity has only one opening for best filling and scraping properties.

A sloping arrangement is consistent with a cavity design narrowing away from the reference surface and, in case of cavities with only one opening, towards its bottom or, differently expressed, that cross-sections taken parallel with the reference surface have decreasing cavity areas when moving away from the reference surface, at least over a part of the cavity depth and preferably over substantially the cavity full depth. It is further preferred that the cavity walls are at least substantially perpendicular but preferably converging towards the cavity bottom, the bottom being the end farthest away form the reference surface. Most preferably small or no undercut parts are present in the cavity.

Discussing next the scraping, the imaginary surface has been described above as an idealized surface entirely continuous with the reference surface. However, in practice any scraping device able to be kept in good contact with the reference surface must have a certain resilience, preferably the minimum resilience necessary for dynamic adaptation to the reference surface, which is preferably made of a harder material, without undue further deformation. Certainly the material in the scraping device should not be soft, in the sense that it easily deforms permanently. Suitable materials may include thermoplastics and preferably elastomers. The scraper resilience means that it will expand by deflection to a certain extent into the cavity volume, thereby creating an actual, or "practical" surface, defining the cavity opening plane for the cavity, generally so as to reduce the cavity volume somewhat. This may not be a problem as long as the reduction is predictable and foreseeable. In order to facilitate such predictability it may be of interest to minimize the volume deviation between the imaginary and practical surfaces, e.g. by having a limited resilience and having a large enough area to cover the entire opening plane so as to entirely cover the cavity opening during some phase of the scraping action.

In summary, in order to strike a balance between the cavity shape design dictated by filling and the design dictated by scraping, it is preferred that the cavity has an elongated opening surface and that the filling direction and the scraping direction have at least a vector component in common, preferably a longer vector component in common and most preferably are substantially parallel. It is further preferred that at least the up-flow, and scraping entrance, cavity end wall has a slow slope whereas other cavity wall are steeper. As indicated, all these observations apply more to larger cavities than to smaller cavities.

Independent of measuring cavity design it is of critical importance to establish true cavity volume so as to enable correct dilution degree and in the end a reliable particles per volume count for a given test sample. Use of a measuring cavity under a reference surface as described makes it difficult to calibrate and utilize only a part of the cavity form measurement, e.g. by level or flow sensors as in alternative measuring methods. Further, when reusing one and the same measuring cavity, e.g. when the cavity forms a part of a reusable measuring instrument, it might be sufficient to measure the cavity once and for all, and calibrate an instrument accordingly, especially if the reused cavity body is designed in high quality materials such as hard metals or ceramics. However, in disposable devices low cost materials are normally selected and random factors, such as temperature or material lot variations, as well as trend factors, such as manufacturing tool wear, tend to create variations in cavity volumes between different, or within a set of, disposable devices. Control over such variations then becomes critical for measurement quality.

Various methods can be used to "measure" a cavity volume. The volume can be measured under the "imaginary" surface, e.g. by laser scanning of cavity three-dimensional extension with integration of volume. The volume can preferably be measured under a "practical" surface as discussed, e.g. by filling a liquid of known particle concentration such as a latex solution into the cavity followed by scraping, possibly by optional dilution, for final counting of particles in known concentration.

As used herein "established" volume has a meaning different from "measured" volume, although established volume is always derived from some kind of measured or "calculated" volume. Certainly each cavity can be measured and the measurement used as established volume also in a system of multiple disposable devices, also referred to herein as a set of "cassettes". However, the volume can also be "estimated". For example it might be sufficient with measurements on less than all cavities in a set of cassettes. If, for example, the cavity bearing parts of the cassettes are of high quality and the corresponding manufacturing tools are wear resistant it might suffice to measure one or a few cavity volumes from each manufacturing tool, or tool part, and rely on this or these measurements as established values for all cavities from the same manufacturing tool or tool part. In case of less high quality materials or long production series from the same tools it is preferred to derive a manufacturing trend for the resulting cavity volumes, e.g. by measuring cavity volumes at intervals, regular or irregular, e.g. in the form of a function or interpolated values, and using the trend to derive an established volume for each individual cavity. Normally a manufacturing tool is worn down in repeated use, resulting in slowly reduced cavity volumes. Finally, in case the manufacturing process and resulting products can be reliably modelled the established cavity volumes can be based on "calculation". In summary an established cavity volume can be based on measurement, estimation or calculations, e.g. as exemplified.

When making measurements, in order to compensate for even small random factors, it is generally preferred to make several measurements and derive a mean, median or similar statistical volume value. This is meaningful only if the volumes have the same nominal or target values, e.g. a volume spread less than 1:2, preferably less than 1:1.5, more preferably less than 1:1.25, and most preferably less than 1:1.1. Such cavity volumes can be presented not only as absolute values but also as deviations from a target or nominal value, e.g. on an information carrier to be read by an instrument.

However, as indicated, a cassette may include cavities of quite different nominal volumes, e.g. for the purpose of providing suitable different dilution degrees for red and white blood counts respectively. This in contrast to the known alternative method of a serially diluting of one and the same sample, first to lower dilution degree, suitable for white blood cell count, followed by dilution of a part, possibly again extracted in a measuring cavity, of the first dilution sample to a second dilution degree, suitable for red blood cell count. In contrast, a parallel dilution to two different dilution degrees from two cavity samples is simpler in terms of steps performed on the cassette. Certainly it is possible to dilute to different degrees from two cavities of the same nominal volume but it is preferred to use a smaller cavity volume for the higher dilution degree in order to keep dilution volumes down on a disposable device. Accordingly it is preferred to provide cavities of at least two, and possibly more, nominal volumes on the cassettes of the invention.

The established cavity volume information can be used for different purposes. A main object of the present invention is to obtain reliable and "defined" dilution degrees for samples measured in the cavities. In connection with blood samples this is important e.g. to obtain true particle counts in the end. In principle dilution degree compensation for cavity volume deviations can be made for example either by adding an adapted amount of dilution media, in order to obtain similar "target" dilution degrees from measuring cavities of different established volumes, or by adding similar dilution media volumes to measuring cavities of different established volumes, to obtain different but "known" dilution degrees, e.g. for allowing recalculation of particle counts. All this is most meaningful between cavities having the same nominal volumes, e.g. within the ranges exemplified above. For high dilution degrees exact volume measurement is more important for the smaller volume part than the larger volume part and in connection with blood testing a blood sample is often diluted more than 10 times, commonly to more than 100 times and often to more than 1000 times or even more than 10000 times, and the precision problems are more severe in connection with direct dilution, in contrast to serial or stepwise dilution.

As indicated a preferred arrangement is to place the measuring cavity on a disposable device, preferably a cassette type of having further features, designed for operative connection to a reusable instrument e.g. having measuring, data processing and/or actuating means, all exemplified in prior art, e.g. WO 03/044488 or WO 2004/045770. It is then possible to provide the instruments with features suitable for the volume compensation described, e.g. by being capable of adding to the sample on the device either an adapted amount of dilution media according to the "target" dilution degree method or by adding a standard amount of dilution media according to the "known" dilution degree method. In either case the instrument can extract the dilution media amount from a reservoir on-board or attached to the instrument or from a reservoir on the cassette. Alternatively and preferably at least a part and preferably all of the dilution media is pre-filled on the cassette, again either a volume adapted to the established cavity volume for that particular cassette according to the "target" method or a standard amount according to the "known" method. Intermediate solutions are also possible such as pre-dilution on the cassette followed by final dilution on the instrument.

In addition to features for adding dilution media, the cassette and/or instrument parts may comprise arrangements for mixing such as for flushing the sample from the measuring cavity and homogenizing the mixture, as known as such in the prior art. It is preferred that at least flushing can be performed on the cassette and preferably also some homogenizing although such features can also be provided on the instrument.

It is preferred that the disposable device, having the measuring cavity, has an information carrier, either arranged for distribution with the device or preferably attached to the device. The information carrier may contain information for human reading only, e.g. for manual correction of test results, but preferably the carrier has information in machine readable form, e.g. for reading by any device, and most preferably the information is readable by a reader on the instrument in a cassette/instrument system, e.g. by being provided in the form of mechanical structures, bar code, magnetic tape, RFID, data chip machine readable text etc. The information can be of any kind, such as type of test to be performed on the device, lot number, expiry date, measuring cavity nominal volume etc.

Preferred information for the present purposes is data relating to necessary compensation for the measuring cavity volume. Such information can be general, e.g. whether or not a compensation action is at all needed from a human operator or the instrument and accordingly which one of several possible modes of operation is expected. For example, in case of cassette onboard dilution media volume compensation, theoretically neither an operator nor the instrument needs to take any compensation action. In case of dilution with a standardized dilution media volume a recalculation of measuring results may be needed. In case of partial dilution on the cassette a complementary dilution might be needed. Accordingly, in a set or population of disposable devices the information carrier can inform about the applicable compensation method or mode of operation expected for each individual device. With preference the information carrier also includes data about the measuring cavity established volume, which data can be presented in many manners for example in the form of an absolute volume value or as a deviation from a nominal value. Such information can be used for any of the compensation method described above, e.g. independent of the instrument for manual or external recalculation or dilution correction, but preferably for data transmission to the instrument for any of the exemplified instrument actions.

It is clear from the above examples that an operative connection between device and instrument may include various features besides necessary mechanical compatibility. Features may be included for information transfer at least from the device to the instrument. Features may be included for transfer of liquid, e.g. sample but preferably diluted sample and possibly rinsing liquid, at least from the device to the instrument, e.g. for measurements, dilution, complementary dilution, mixing, rinsing of the instrument etc., but preferably also back to the device, e.g. for disposal of sample contaminated liquid such as diluted sample and instrument rinsing liquid. Features may be included for instrument actuation of device process operations, such as scraping action, flushing, mixing, liquid transfer to the instrument etc.

With reference to FIG. 1-5c different embodiments of a known device for extraction of partial defined sample volume from a larger liquid sample volume is shown. An information carrier (not shown) is applied to or arranged for distribution with said device.

Figure 1A:
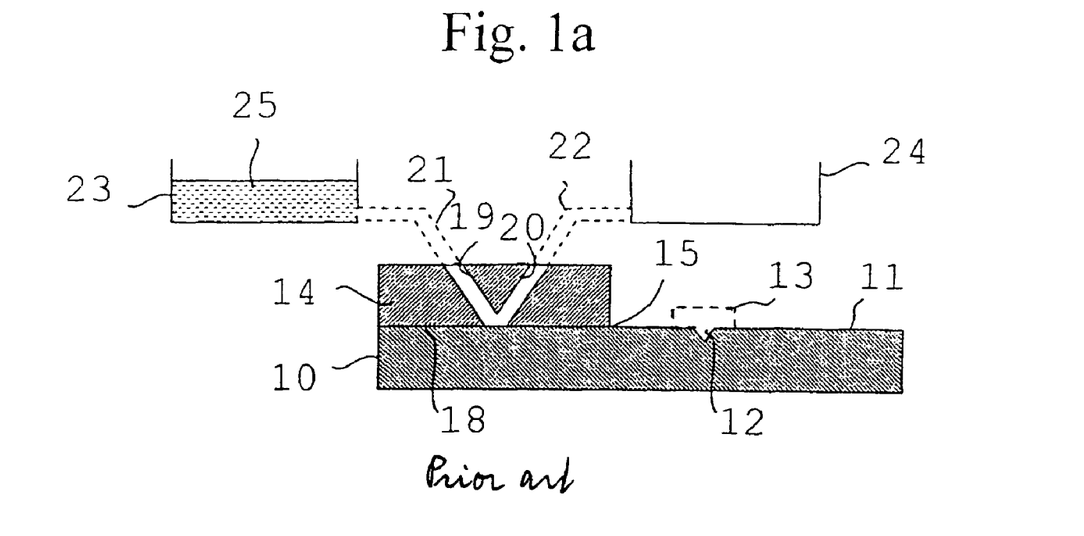
FIGS. 1a and 1b are schematic sectional views showing the principle of a known device for extraction of a sample volume from a larger volume according to the invention shown in a first and a second position, respectively.
Figure 1B:
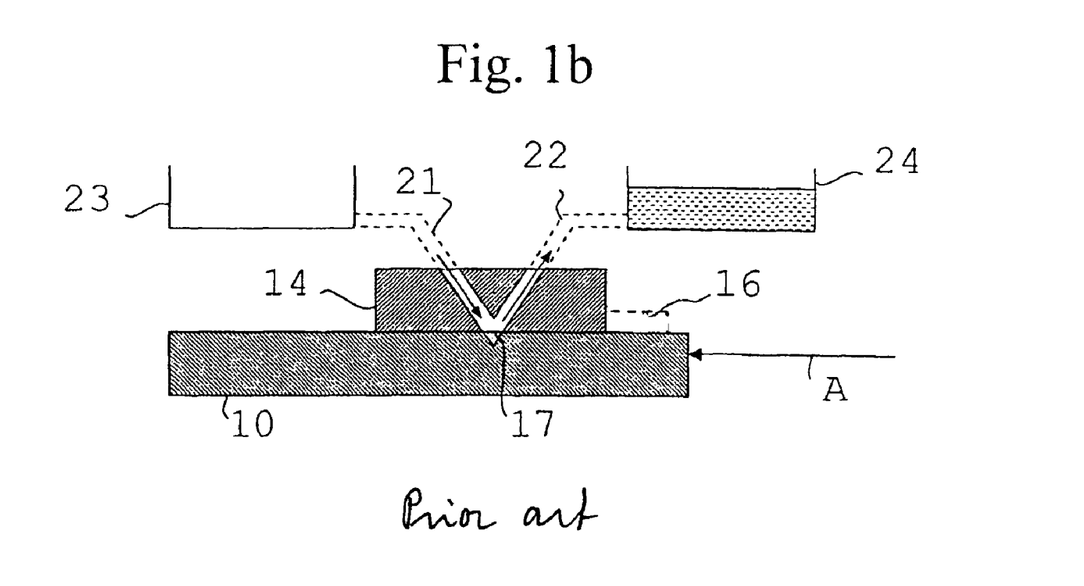

FIGS. 1a and 1b show a first body 10 that has a reference surface 11 in which is provided a cavity 12 having an accurately defined, small volume. A relatively large volume 13 of a sample, such as a blood sample, is applied onto the reference surface 11 such that it is ensured that the cavity is filled with sample.

A second body, scraper, 14 has an edge 15 abutting the reference surface 11 of the first body. The bodies 10 and 14 are relatively slidable along the reference surface 11 as indicated by an arrow A, so that the edge, upon passing the cavity, scrapes or shears off a volume 16 of the sample along the reference surface 11 leaving just the accurately defined, small sample volume 17 within the cavity 12. This situation is shown in FIG. 1b.

In practice, the second body 14 has a surface 18 starting at the edge 15 and facing and abutting the reference surface 11 of the first body in a fluid tight manner. For the purpose of diluting the accurately defined, small sample volume 17, two channels 19, 20 extend through the second body and open in its surface 18 at positions enabling respective fluid communication with the cavity 12 as shown in FIG. 1b. The channels are shown here to extend in a V-shaped, converging manner towards the surface 18. Evidently, the channels may extend in other directions towards the surface 12 and the cavity 12 therein, including mutually parallel channel directions.

Conduits 21, 22, indicated by broken lines, connect a respective one of the channels 19, 20 with a respective one of receptacles 23, 24. The receptacle 23 is shown in FIG. 1a to contain a defined volume of a liquid 25, such as a diluent or a lysing agent. When the first and second bodies are in the relative position shown in FIG. 1b, flow from the receptacle 23 through the conduit 21 will be directed into the cavity 12, thereby flushing its volume 17 of sample and bringing it through the conduit 22 into the receptacle to provide therein a volume of diluted sample having a defined dilution ratio. The volume of diluted sample may be brought to flow several times forth and back between the two receptacles to ensure proper mixing and dilution, but tests have shown that already one flushing provides a satisfactory result.

Depending on the kind of test to be performed and the dilution ratio desired, the cavity may typically have a volume of between 0.05 and 10 µl, even if it is quite possible to provide cavity volumes of, e.g., between 0.02 and 20 µl.

In practice, it may be useful to provide more than one cavity in the surface of the body 10, for instance one relatively small cavity (e.g. 0.05 µl) and one relatively large cavity (e.g. 10 µl), thereby enabling simultaneous dilution into two different dilution ratios. This is the preferred embodiment of the invention as regards blood analysis.

Figure 2:
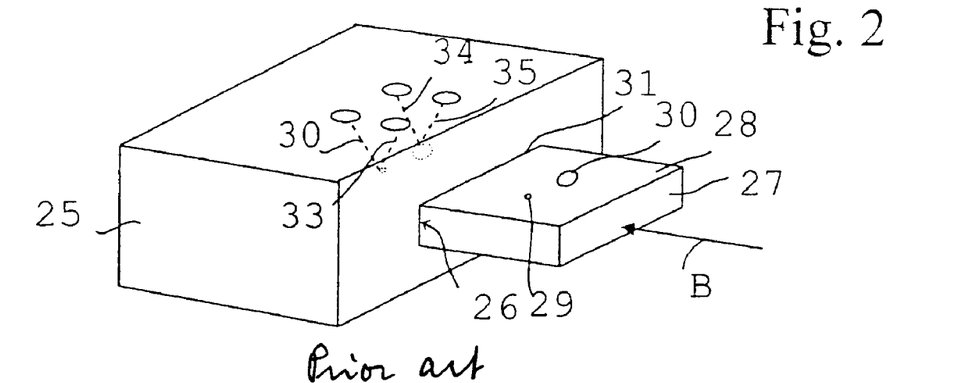
FIG. 2 is a perspective view schematically showing a first principal embodiment of the known device.
Figure 3:
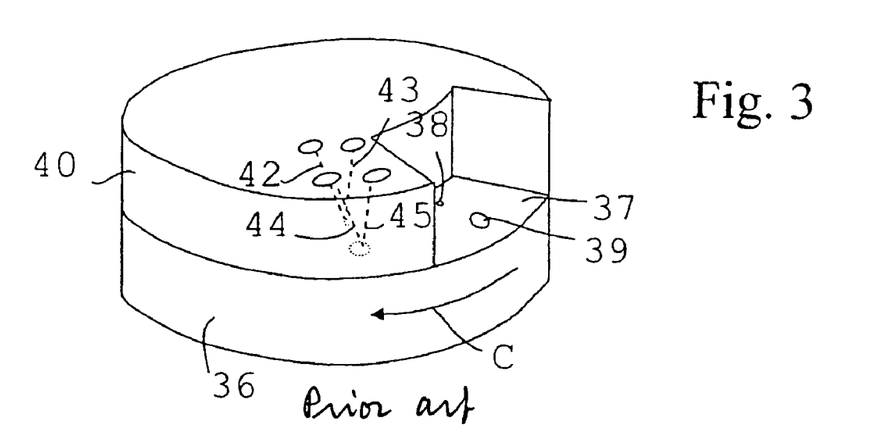
FIG. 3 is a similar view showing a second principal embodiment of the known device.
Figure 4:
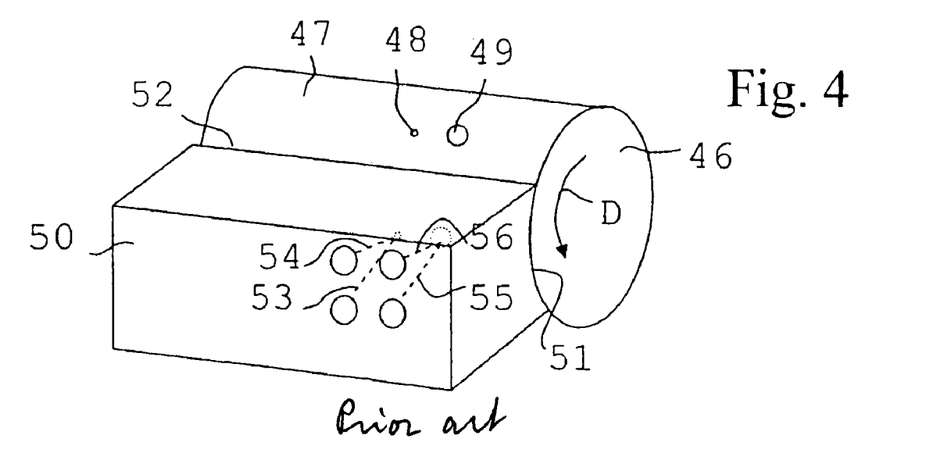
FIG. 4 is a similar view showing a third principal embodiment of the known device.

Examples of prior art devices embodying this possibility are shown in FIGS. 2-4.

The embodiment of FIG. 2 comprises a block-shaped housing 25 (second body) having therein a slot 26. A slide 27 (first body) has in an upper reference surface 28 a smaller cavity 29 and a larger cavity 30. The slot has an edge 31 closely abutting the surface 28. Two pairs of converging channels 32, 33 and 34, 35 extend through the housing 25 and open in a surface of the slot 26 at respective locations corresponding to the positions of the cavities 29, 30. Thus, a non-shown, lager volume of a sample applied onto the reference surface 28 will be sheared off by the edge 31 upon sliding the slide 27 into the slot as indicated by an arrow B, leaving two accurately defined volumes of sample in the cavities 29 and 30 to be diluted as explained in connection with FIGS. 1a and 1b.

In FIG. 3, the first body is a disc-shaped body 36 having in a reference surface 37 a smaller cavity 38 and a larger cavity 39. The second body is likewise a disc-shaped body 40 having at its circumference a cut-out portion providing access to the surface 37 of the first body and also providing at least one edge 41 abutting the reference surface 37. Two pairs of converging channels 42, 43 and 44, 45 extend through the body 40 and open in its surface abutting the body 36 at respective locations corresponding to the positions of the cavities 38, 39. Thus, a non-shown, lager volume of a sample applied onto the surface reference 37 will be sheared off by the edge 41 upon relatively rotating the two bodies as indicated by an arrow C, leaving two accurately defined volumes of sample in the cavities 38 and 39 to be diluted as explained in connection with FIGS. 1 and 2.

In FIG. 4, the first body is a cylindrical body 46 having in its peripheral reference surface 47 a smaller cavity 48 and a larger cavity 49. The second body is a block-shaped body 50 having one surface 51 concavely shaped in conformity with the cylindrical reference surface 47. An edge 52 of the surface 51 abuts the reference surface 47. Two pairs of converging channels 53, 54 and 55, 56 extend through the body 50 and open in its surface 51 abutting the body 46 at respective locations corresponding to the positions of the cavities 48, 49. Thus, a non-shown, larger volume of a sample applied onto the reference surface 47 will be sheared off by the edge 52 upon relatively rotating the two bodies as indicated by an arrow D, leaving two accurately defined volumes of sample in the cavities 48 and 49 to be diluted as explained in connection with FIGS. 1a and 1b.

Figure 5:
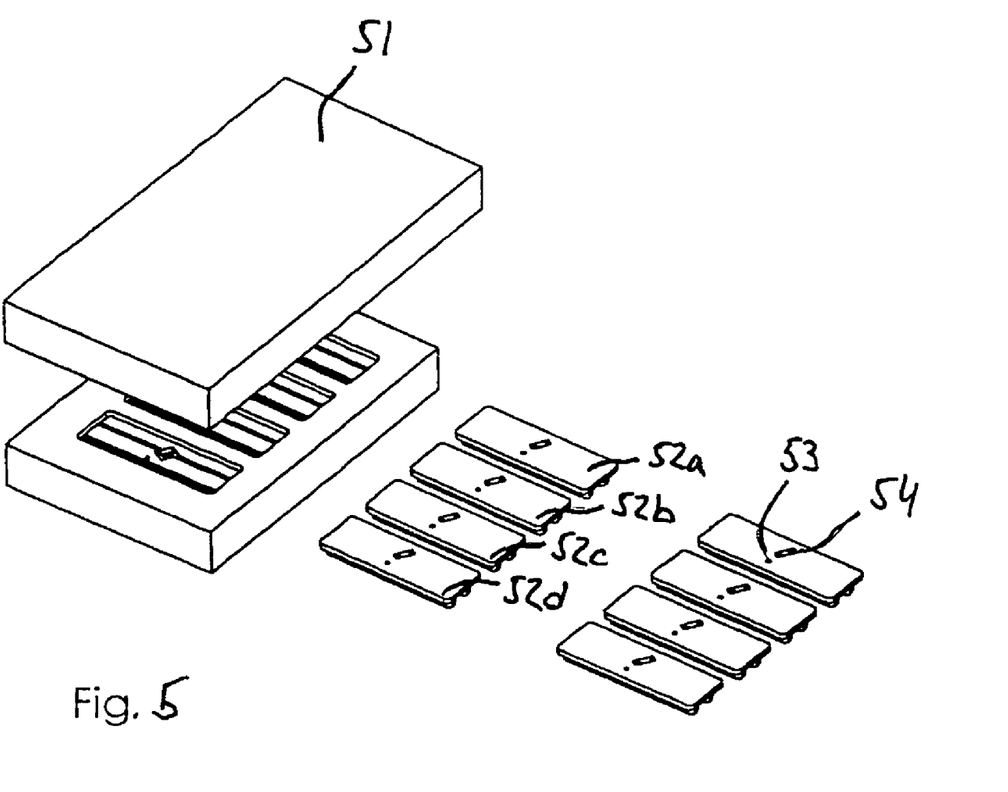
FIG. 5 is a schematic view of a moulding machine with four moulding tools showing the manufacturing of a device for extraction of a sample volume from a larger volume according to the invention provided with two cavities, inherently said cavities having small variations in volume.
Figure 6:
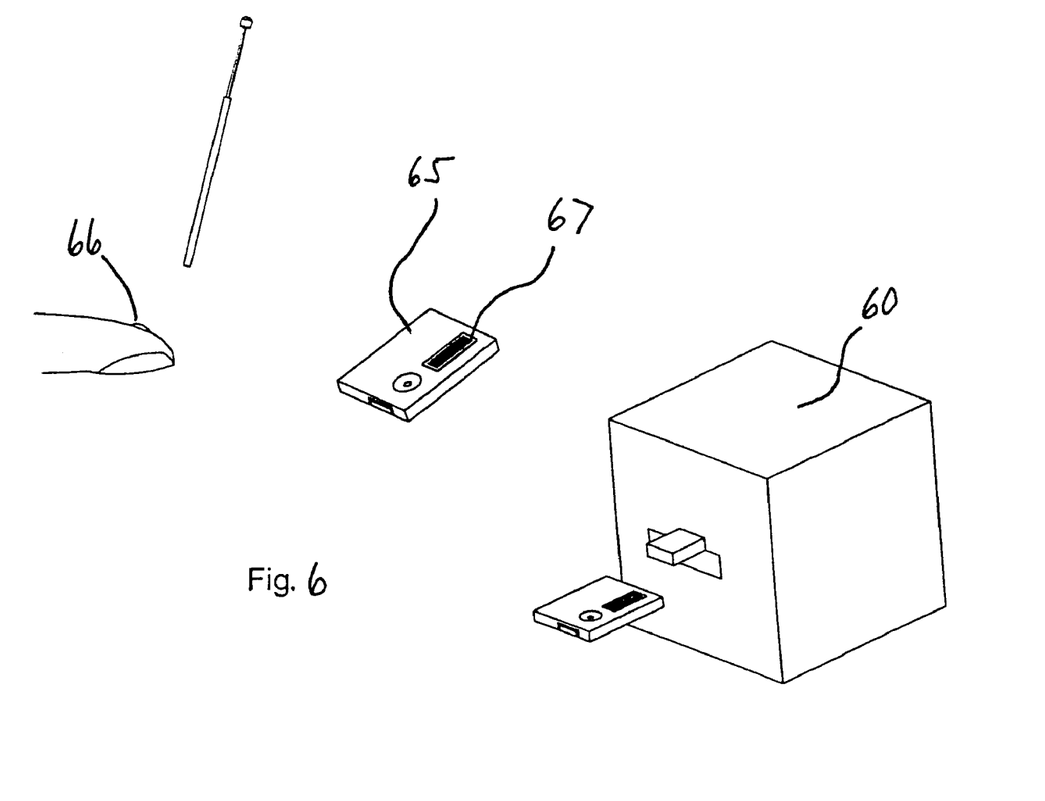
FIG. 6 shows a blood test taken from a the finger of a person to be transferred to a blood testing cassette to be placed in a blood cell counting apparatus (schematically shown); the cassette being provided with a volume variation information carrier.

FIG. 5 shows schematically an injection moulding machine 51 with four moulding tools (not shown) for the manufacturing of sampling bodies 52a, 52b, 52c, and 52d, each provided with at least one cavity. In the example shown two cavities 53, 54 are provided in one sampling body. When moulding sampling bodies the cavities will have small variations in volume. One such sampling body forms part of blood testing cassette 65 to be placed in an analytical instrument 60 (FIG. 6). Although, in the description below reference is made to a moulding machine with four moulding tools, it is obvious for the man skilled in the art that the moulding machine can have 2, 4, 6, 8 or even more moulding tools.

In the case the sampling body is provided with two cavities 53, 54 for simultaneously counting both white and red cells, a cassette 65 is provided with two chambers (not shown) filled with a dilution or lysing agent and two empty chambers (not shown), whereby one filled chamber is in fluid communication with one cavity of the sampling body filled with the blood sample and one empty chamber. By this arrangement the accurately defined blood sample can be mixed with the dilution or lysing agent and diluted to a dilution ratio range of about 1:100 to 1:80000 within the cassette 65.

The typical nominal volume of the cavities 53, 54 in the sampling body is within the range of about 0.01-0.5 µl, preferably about 0.1 µl, and about 1-10 µl, preferably 5 µl, respectively. Due to the large dilution ratio even small variations in the volumes of the cavities 53, 54 of different sampling bodies 52a, 52b, 52c, 52d will greatly influence the result of the cell counting.

Although the volume of the cavities 53, 54 from each moulding tools is approximately the same during a batch of sampling bodies, the respective cavity of sampling bodies 52a, 52b, 52c, and 52d will have different volumes.

To be able to carry out the invention a number of cavity volumes are measured so as to obtain volume information of the cavity volume sought.

According to the invention these variations in volume between cavities from different sampling bodies 52a from the same moulding tools and from sampling bodies 52a, 52b, 52c, and 52d from different moulding tools are measured and used to improve the results of blood cell counting analyses.

These variations in volume can also be expressed as, for instance, an absolute volume value, a deviation from a nominal volume value of the small cavity and the large cavity, respectively.

Thus, according to the invention by knowing these variations in cavity volume an established value of the cavity volume sought can be determined, and the cassette or blood sample volume defining device 65 can thereby be provided with any type of volume information carrier 67, as seen in FIG. 6.

Thus, as seen in FIG. 6, a blood sample is taken from the finger of a person by a syringe, for instance, and transferred to the device 65 provided with the volume information carrier 67. The volume information is coded in machine readable form, for instance, and comprises a bar code, a magnetic code, an electronic memory, machine readable text, a radio frequency identification device (RFID) or similar means, showing the established value which can be read by any suitable arrangement. The device 65 is then inserted into the instrument 60 and the well defined volume of the blood sample is diluted by and mixed with diluent and/or lysing agent to the desired dilution ratio.

Moreover, in another embodiment (not shown) the device is adapted to be connected to an analytical instrument via conducting arrangements for transferring sample and/or diluent containing liquid to the instrument. Also the volume information is transferred to the instrument by suitable means.

The information carrier 67 mentioned above is used for compensation variations in the volume of cavities 53, 54 of different sampling bodies. Said information carrier 67 can also contain other information such as batch number, best-before date, information about the type and volumes of the diluent and/or lysing agent, and so forth.

To be able to perform the measuring it is necessary to define the physical location and form of the opening plane. This is done on one hand by moving a scraper along and in contact with reference surface over the cavity, or on the other hand by interpolating the opening plane from an optical detection of the reference surface surrounding the opening plane.

The measuring of the cavity can also be done by filling an excess liquid amount in the cavity and moving the scraper along and in contact with the reference surface over the cavity, which liquid left in the cavity is then compared with a reference cavity of known volume.

Another way of measuring the cavity volume is by optical detection of said volume and possible subtraction of the volume above the opening plane. Preferably the established volume is the measured volume value, or the mean value of the measured value.

Another possible way of estimating the cavity volume is to measure the changing trend for several devices and assigning established volume values to the several devices based on the trend.

As is obvious for the man skilled in the art the measured volume value can be obtained for more then one cavity in the reference surface, and the more than one cavity have the same nominal target volumes. Preferably, the measured volume values lie within a range of 1:2.

Figure 7:
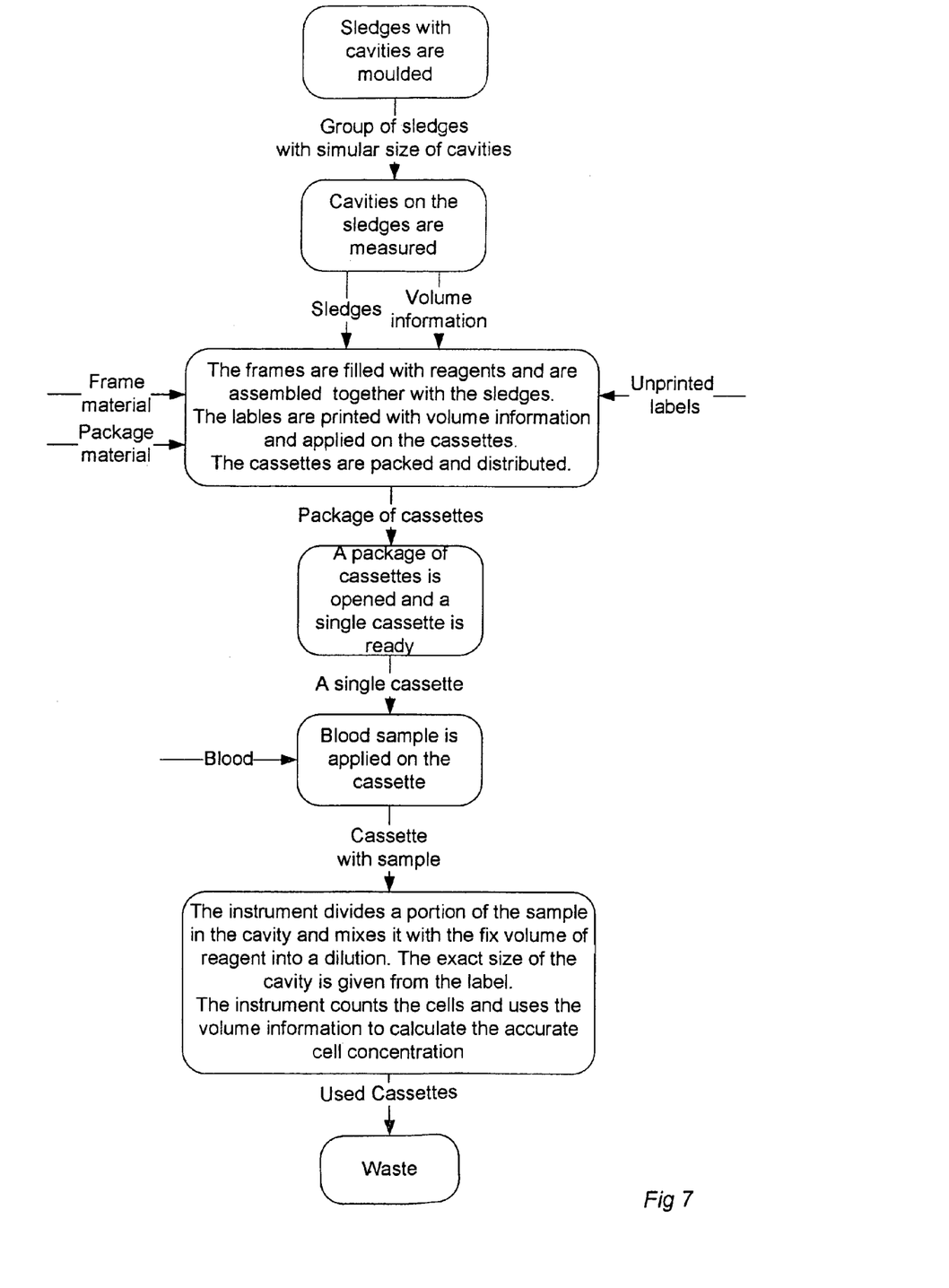
FIG. 7 is a flow chart describing the different steps carried out from obtaining the sampling bodies with cavities to the blood analyses conducted.
Figure 8:
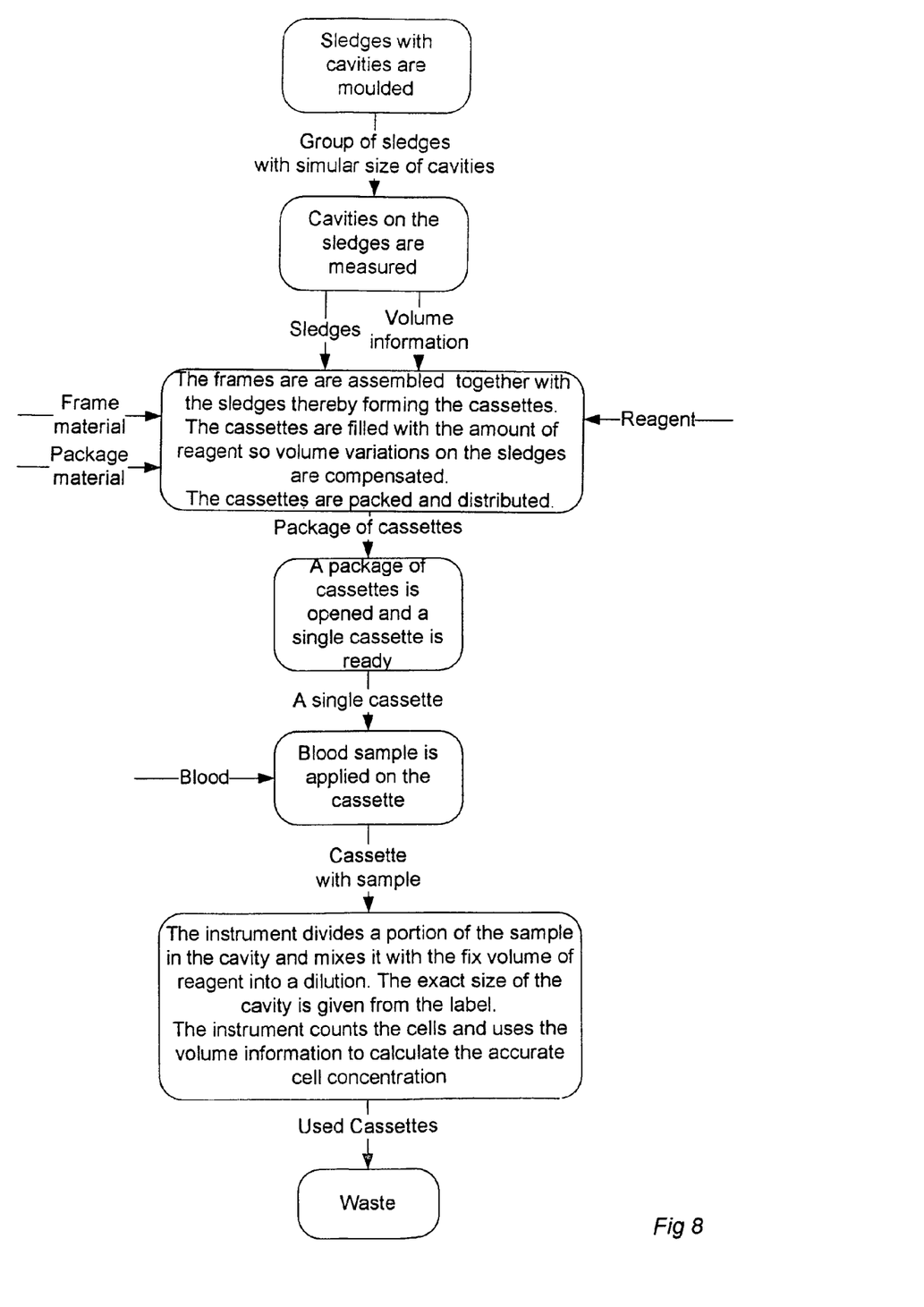
FIG. 8 is another flow chart describing the different steps carried out from obtaining the sampling bodies with cavities to the blood analyses conducted.

FIGS. 7 and 8, respectively, is a flow chart showing two different aspects to carry out the invention.

In FIG. 7, showing the first aspect, sampling bodies 52a, 52b, 52c, and 52c with cavities 53, 54 are made by different moulding tools by injection-mould, for example, of a suitable plastic material. The sampling bodies from the same moulding tools are grouped and the respectively cavity of the sampling bodies is measured by known means so as to obtain an average volume or a value of the volume deviation of the respectively cavity of the samplings bodies from the same moulding tools.

Then the sampling bodies are assembled with pre-formed frameworks, preferably made of the same plastic material as the sampling bodies, so as to form cassettes. At least one particularly dedicated chamber made in the framework is pre-filled with an accurate volume of diluent and/or lysing agent and has fluid communication through channels made in the framework and via the respectively cavity with at least one empty chamber made in the framework. Thus, by this arrangement it is possible to mix the diluent and/or lysing agent with the blood sample in said at least one cavity. Volume information carriers in the form of labels printed with exact volume information of the respectively cavity of the assembled framework are applied to the cassettes.

The cassettes are packed in suitable package material and distributed for storage or to the final user.

The second aspect, shown in FIG. 8, differs from the first aspect in that the frames and the sampling bodies are assembled together forming cassettes. The at least one chamber containing the diluent or lysing agent is filled with said agent to such an amount for obtaining the extent of dilution of the blood sample sought.

When a blood sample is to be take and analysed the final user opens a cassette, and the blood sample is introduced into the cassette by known methods as taught in, for instance, the non-published Swedish patent application No. 0500784-4, and at least one accurately defined blood sample volume in the cavity of the body is obtained and brought into communication with the diluent and/or lysing agent in the cassette.

The cassette is then placed in the blood counting apparatus which mixes said at least one accurately defined blood sample volume with the diluent and/or lysing agent. The apparatus counts the blood cells and reads the information regarding the exact volume of the cavity from the label, which information is used to calculate, by suitable means, the dilution ratio and thus the accurate blood cell concentration. Thereafter the cassette is removed from the apparatus and disposed of.

The invention claimed is:

1. A device for extraction of a partial defined sample volume from a larger liquid sample volume comprising a) a body having a reference surface and b) a measuring cavity extending from a part of the reference surface into the body, thereby forming at least one opening plane substantially uniform with the reference surface, the cavity having a defined volume below said opening plane in said reference surface, the body being adapted for reception of an excess sample volume at the cavity and elimination of sample above the reference surface to leave in the cavity a measured sample volume having said defined volume, said device comprising an information carrier, applied to or arranged for distribution with the device, having direct or indirect volume information about the defined volume established for the cavity.

2. The device of claim 1, characterized in that the volume information is coded in machine readable form.

3. The device of claim 2, characterized in that the volume information is coded in the form of bar-code, magnetic code, electronic memory and/or machine readable text or a RFID-chip.

4. The device of claim 1, characterized in that the volume information is coded as an absolute volume value.

5. The device of claim 1, characterized in that the volume information is coded as a deviation from a nominal volume value.

6. The device of claim 1, characterized in that the device is arranged for operative connection to an analytical instrument.

7. The device of claim 6, characterized in that the operative connection comprises transferring arrangements for transfer of the coded volume information to the instrument.

8. The device of claim 1, characterized in a removal arrangement adapted for the elimination of sample above the reference surface.

9. The device of claim 8, characterized in that the removal arrangement comprises a scraper adapted for movement along and in contact with the reference surface.

10. The device of claim 1, characterized in that the reference surface is substantially flat.

11. The device of claim 1, characterized in that the cavity has only one opening.

12. The device of claim 1, characterized in more than one cavity arranged in the body.

13. The device of claim 1, characterized in that the body is made of plastic material.

14. A method for determining the volume of at least one cavity, and optionally further cavities, arranged for extraction of a partial defined sample volume from a larger liquid sample volume, the one cavity, and optional further cavities each, being arranged in a device comprising a) a body having a reference surface and b) a measuring cavity extending from a part of the reference surface into the body, thereby forming at least one opening plane substantially uniform with the reference surface, the cavity having a defined volume below said opening plane in said reference surface, the body being adapted for reception of an excess sample volume at the cavity and elimination of sample above the reference surface to leave in the cavity a measured sample volume having said defined volume, said method comprising:

measuring a volume corresponding to the cavity confined by the opening plane and body surfaces surrounding the measuring cavity to obtain a measured volume value and deriving an established volume value from the measurement.

15. The method of claim 14, characterized in that the measuring comprises filling of an excess liquid amount in the cavity and moving a scraper along and in contact with the reference surface over the cavity.

16. The method of claim 15, characterized in that the measuring further comprises comparing the liquid left in the cavity after scraping with a reference cavity of known volume.

17. The method of claim 14, characterized in producing several devices by the same cavity forming tool and obtaining measured volume values for cavities from at least some of the several devices.

18. The method of claim 17, characterized in estimating a cavity volume changing trend for the several devices based on the measured volume values and assigning established volume values to the several devices based on the trend.

19. The method of claim 14, characterized in applying to or distributing with the one device or at least one further device an information carrier having information about the established volume value.

20. The method of claim 19, characterized in that the volume information is coded in machine readable form.

* * * * *

UNITED STATES PATENT AND TRADEMARK OFFICE
CERTIFICATE OF CORRECTION

| | | |
|---|---|---|
| PATENT NO. | : 8,033,186 B2 | Page 1 of 1 |
| APPLICATION NO. | : 12/444394 | |
| DATED | : October 11, 2011 | |
| INVENTOR(S) | : Ingemar Berndtsson and Tommy Andersson | |

It is certified that error appears in the above-identified patent and that said Letters Patent is hereby corrected as shown below:

On the Title Page, Item [54] and in the Specification, Column 1, Line 1, change the Title to
-- DEVICE FOR EXTRACTION OF A DEFINED SAMPLE VOLUME FROM A LARGER VOLUME --.

In the Specifications:

Column 1, line 19, delete the word "partially".

Signed and Sealed this
Sixteenth Day of July, 2013

Teresa Stanek Rea
*Acting Director of the United States Patent and Trademark Office*